(12) United States Patent
Kankan et al.

(10) Patent No.: US 8,658,821 B2
(45) Date of Patent: Feb. 25, 2014

(54) PROCESS FOR THE PREPARATION OF NATEGLINIDE

(75) Inventors: Rajendra Narayanrao Kankan, Mumbai (IN); Dharmaraj Ramachandra Rao, Mumbai (IN); Manjinder Singh Phull, Mumbai (IN); Dilip Ramdas Birari, Thane (IN)

(73) Assignee: Cipla Limited, Mumbai (IN)

( * ) Notice: Subject to any disclaimer, the term of this patent is extended or adjusted under 35 U.S.C. 154(b) by 1590 days.

(21) Appl. No.: 11/570,405

(22) PCT Filed: Jun. 8, 2005

(86) PCT No.: PCT/GB2005/002267
§ 371 (c)(1),
(2), (4) Date: Feb. 28, 2007

(87) PCT Pub. No.: WO2005/121071
PCT Pub. Date: Dec. 22, 2005

(65) Prior Publication Data
US 2007/0259955 A1  Nov. 8, 2007

(30) Foreign Application Priority Data
Jun. 11, 2004 (GB) .................... 0413084.5

(51) Int. Cl.
*C07C 229/36* (2006.01)

(52) U.S. Cl.
USPC ........................................ 562/450

(58) Field of Classification Search
CPC .......................... C07C 2101/14; C07C 231/04
See application file for complete search history.

(56) References Cited

U.S. PATENT DOCUMENTS

| | | | | |
|---|---|---|---|---|
| 4,816,484 A | | 3/1989 | Toyoshima et al. | |
| 5,122,610 A | * | 6/1992 | Henning et al. | 530/331 |
| 5,201,932 A | * | 4/1993 | Maywald et al. | 504/271 |
| 5,463,116 A | | 10/1995 | Sumikawa et al. | |

FOREIGN PATENT DOCUMENTS

| | | | |
|---|---|---|---|
| EP | 1334963 A1 | | 8/2003 |
| IN | WO 03/093222 A1 | * | 11/2003 |
| WO | WO2004/005240 A1 | | 1/2004 |
| WO | WO2004/018408 A1 | | 3/2004 |

OTHER PUBLICATIONS

Carey et al, Advanced Organic Chemistry, 4th Edition, Part B, 2001, Kluwer Academic/Plenum Publishers, New York, New York, pp. 172-179.*
Shinkai, Hisashi, et al., "N-(Cyclohexylcarbonyl)-D-Phenylalanines and Related Compounds. A New Class of Oral Hypoglycemic Agents. 2," Journal of Medicinal Chemistry, vol. 32, 1989, American Chemical Society, pp. 1436-1441.
Wang, Dun, et al., "Synthesis of new nateglinide as a new antidiabetic drug," Chinese Journal of Medicinal Chemistry, vol. 12, No. 2, Apr. 2002, pp. 94-96.

(Continued)

*Primary Examiner* — Paul A Zucker
(74) *Attorney, Agent, or Firm* — Conley Rose, P.C.; Rodney B. Carroll

(57) ABSTRACT

A one-pot process for the preparation of nateglinide, which process comprises reacting an alkyl ester of D-phenylalanine of formula (II):

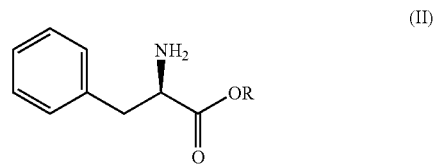

(II)

where R represents $C_{1-4}$ alkyl, typically methyl, either as the free base or in salt form (typically the hydrochloride), with trans-4-isopropylcyclohexanecarboxylic acid of formula (III):

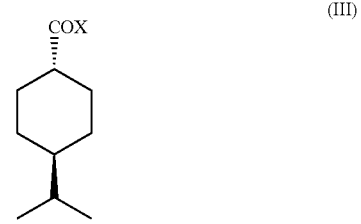

(III)

where X represents hydroxy or halo, typically chloro, to obtain a $C_{1-4}$ alkyl ester of nateglinide of formula (IV), preferably the methyl ester of nateglinide:

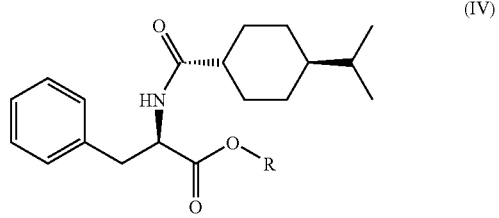

(IV)

followed by hydrolysis to yield nateglinide of formula (I):

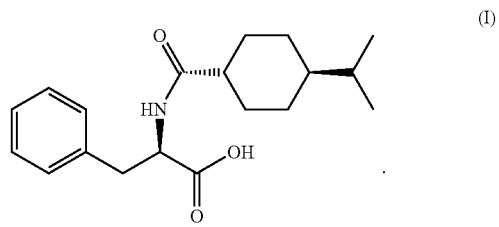

(I)

12 Claims, 3 Drawing Sheets

(56) References Cited

OTHER PUBLICATIONS

Foreign communication from a related counterpart—International Search Report, PCT/GB2005/002267, Jul. 26, 2005, 4 pgs.

Foreign communication from a related counterpart—International Preliminary Report on Patentability, PCT/GB2005/002267, Oct. 6, 2006, 7 pgs.

* cited by examiner

PROCESS FOR THE PREPARATION OF NATEGLINIDE

CROSS-REFERENCE TO RELATED APPLICATIONS

This application is a filing under 35 U.S.C. 371 of International Application No. PCT/GB2005/002267 filed Jun. 8, 2005, entitled "Process for the Preparation of Nateglinide," claiming priority of Great Britain Patent Application No. GB 0413084.5 filed Jun. 11, 2004, which applications are incorporated by reference herein in their entirety.

FIELD OF THE INVENTION

The present invention is concerned with a one-pot process for the preparation of nateglinide, nateglinide prepared thereby, compositions containing the same, therapeutic uses thereof and methods of treatment employing the same.

BACKGROUND OF THE INVENTION

N-(trans-4-isopropyl cyclohexylcarbonyl)-D-phenylalanine, generally known as nateglinide, is an antidiabetic drug used as a hypoglycemic agent in patients with type II diabetes. Nateglinide has the following structural formula:

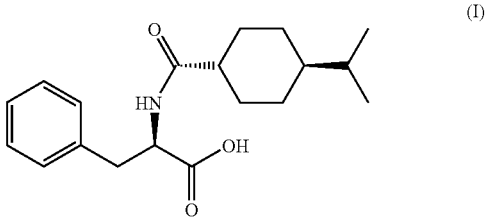

(I)

The synthesis of nateglinide is previously described in U.S. Pat. No. 4,816,484, and employs the activated N-hydroxy succinimide ester of trans-4-isopropyl cyclohexanecarboxylic acid as an intermediate for condensation with a D-phenyl alanine alkyl ester. The alkyl ester of nateglinide shown below, where R is an alkyl group, is obtained after reaction between the above referred to activated ester of trans-4-isopropyl cyclohexanecarboxylic acid and a D-phenyl alanine alkyl ester

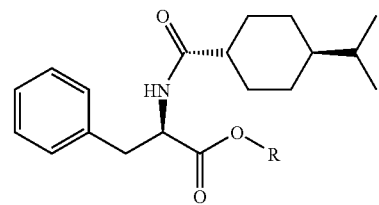

It is taught by U.S. Pat. No. 4,816,484 that the above alkyl group acts as a protecting group, limiting the amount of undesirable side reactions. The overall process described in U.S. Pat. No. 4,816,484 for the preparation of nateglinide can be represented as follows:

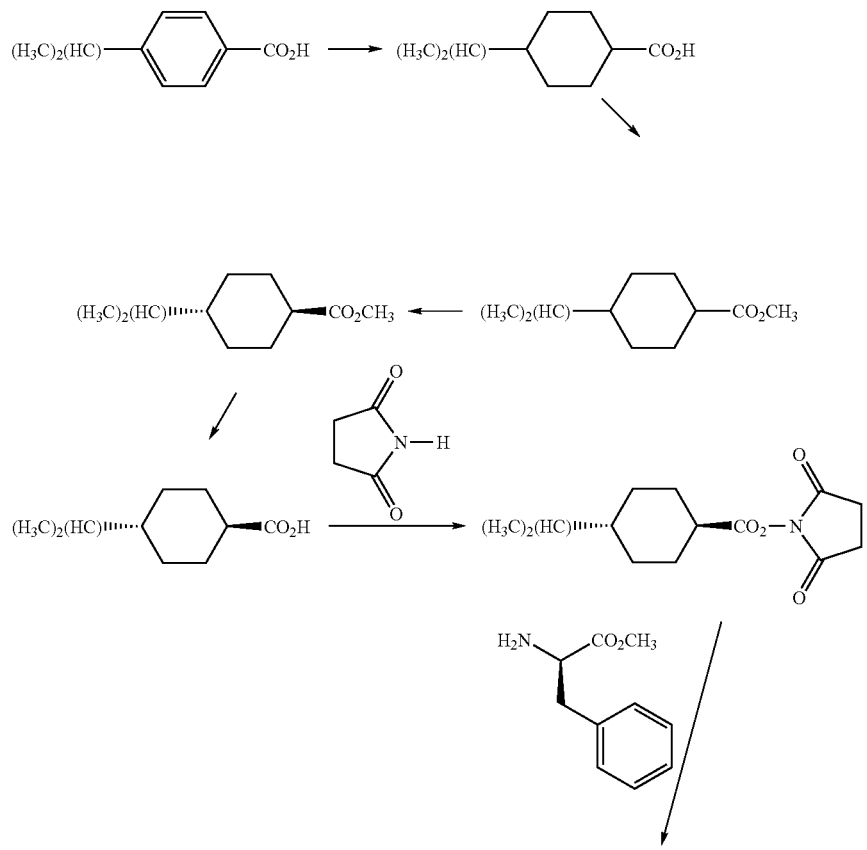

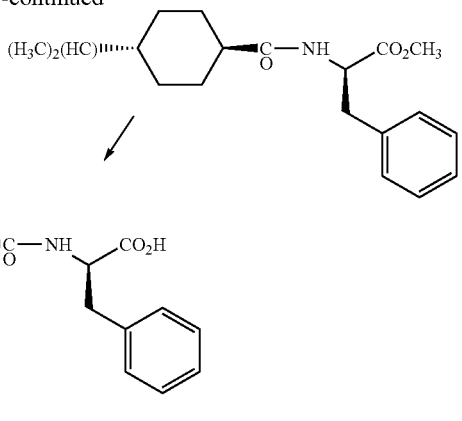

(I)

However, it has now been found that by following the process as described in U.S. Pat. No. 4,816,484, the nateglinide ester is found to be present in an undesirable amount in the final nateglinide product. Also, crystallization of nateglinide from aqueous methanol results in undesirable further esterification.

Chinese Journal of Medicinal Chemistry, Vol. 12, page no: 94, describes the synthesis of trans-4-isopropylcyclohexane carboxylic acid through reduction of 4-isopropylbenzoic acid, which on reaction with N-hydroxyphthalimide in presence of N'N'-dicyclohexylcarbodiimide gives the activated N-hydroxyphthalimide ester. This is subjected to acylation reaction with D-phenylalanine ethyl ester, and subsequent hydrolysis gives nateglinide.

Journal of Medicinal Chemistry, 1989, Vol. 32, No. 7, page no: 1437, describes the reaction of trans-4-isopropylcyclohexane carboxylic acid with dicyclohexylcarbodiimide and N-hydroxysuccinimide to form the activated N-hydroxysuccinimide ester. This is then reacted with D-phenylalanine methyl ester, and subsequent hydrolysis gives nateglinide.

PCT Application WO2004/018408 describes a method for the synthesis of nateglinide which includes reacting trans-4-isopropylcyclohexane carboxylic acid with an alkyl chloroformate of the formula $ClCO_2R$, where R is an alkyl group, to form a trans-4-isopropylcyclohexane mixed acid anhydride. The mixed acid anhydride is then reacted with an aqueous alkali salt solution of D-phenylalanine to yield a reaction mixture including nateglinide.

U.S. Pat. No. 5,463,116 discloses stable crystals of nateglinide. The nateglinide is first produced according to the method described in Example 3 of Japanese patent application laid open no. 63-54321 (an equivalent of U.S. Pat. No. 4,816,484).

EP1334963A discloses a method for producing nateglinide crystals from a reaction mixture containing nateglinide. The nateglinide is obtained by reacting trans-4-isopropylcyclohexane carboxylic acid chloride with D-phenylalanine in a mixed solvent of a ketone and water in the presence of an alkali, followed by neutralisation with an acid. Specific adjustment of the temperature of the mixture and the concentration of ketone solvent results in precipitation of nateglinide crystals. The ketone solvent(s) in the reaction is usually essential to proceed the reaction. However, a large quantity of acetone in the reaction causes high proportion of by-product.

PCT Application WO 2004/005240 describes a process for the preparation of nateglinide by reacting trans-4-isopropyl cyclohexane carboxylic acid chloride with a suitable salt of D-phenyl alanine in presence of an effective amount of an organic amide.

D-phenylalanine used as the starting material in the processes of EP1334963A and WO 2004/005240 is not protected by an alkyl group, so reaction of the unprotected carboxylic acid group leads to undesirable side products.

There exists a need for improved processes for the preparation of nateglinide.

SUMMARY OF THE INVENTION

Figure 1:
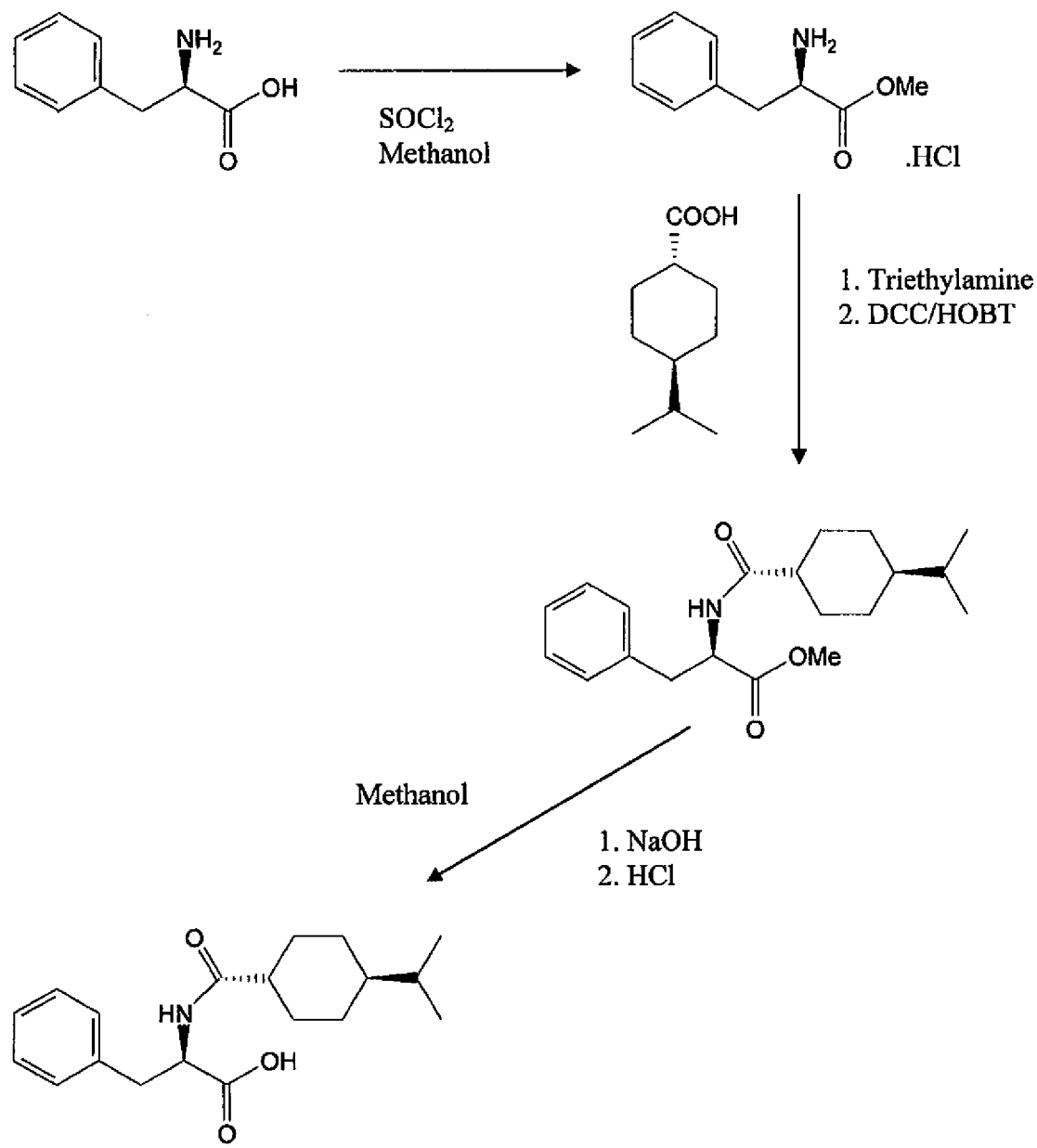
FIGS. 1-3 depict embodiments of reaction schemes for the preparation of nateglinide.

According to the present invention, therefore, there is now provided a one-pot process for the preparation of nateglinide, which process comprises reacting an alkyl ester of D-phenylalanine of formula (II):

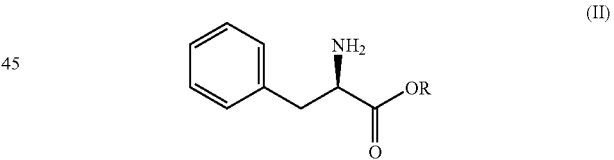

(II)

where R represents $C_{1-4}$alkyl, typically methyl, either as the free base or in salt form (typically the hydrochloride), with trans-4-isopropylcyclohexanecarboxylic acid or trans-4-isopropylcyclohexanecarboxylic acid halide of formula (III):

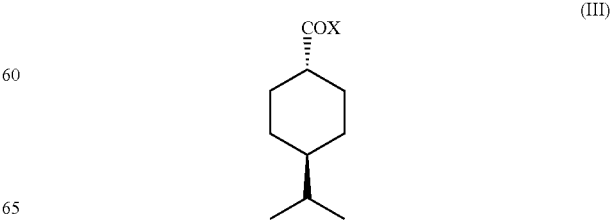

(III)

where X represents hydroxy or halo, typically chloro, to obtain a $C_{1-4}$ alkyl ester of nateglinide of formula (IV), preferably the methyl ester of nateglinide:

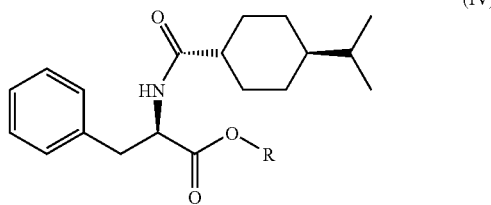

(IV)

followed by hydrolysis to yield nateglinide of formula (I):

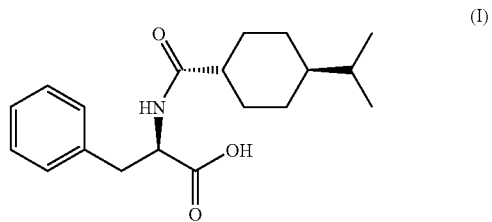

(I)

The two key intermediates required in the preparation of nateglinide are D-phenyl alanine and trans-4-cyclohexane carboxylic acid. It will be appreciated from the above overall reaction scheme provided for U.S. Pat. No. 4,816,484 that this known synthesis involves a multi-step process comprising (a) esterification of D-phenyl alanine to get the ester as a hydrochloride, (b) releasing the free base, (c) preparing an active ester of trans-4-isopropylcyclohexane carboxylic acid, (d) coupling of (b) and (c) and finally (e) hydrolysis of the nateglinide ester to nateglinide. The present invention has, however, eliminated the part (c) of the process and combined the other four steps into a one-pot process. The present invention further provides a process to obtain pure nateglinide directly from the reaction, with removal of impurities being achieved by washing a solution of nateglinide in water with an organic solvent prior to its isolation substantially as hereinafter described in greater detail.

A process according to the present invention preferably further comprises initially reacting D-phenyl alanine with a solution of thionyl chloride in a $C_{1-4}$alcohol, preferably methanol, to give the corresponding alkyl ester of formula (II), preferably the methyl ester, as the hydrochloride salt, which can either be reacted directly with trans-4-isopropylcyclohexanecarboxylic acid of formula (III) or can be converted to the free base prior to reaction therewith.

DETAILED DESCRIPTION OF THE INVENTION

According to a preferred first embodiment of the present invention, a process as provided thereby further comprises initially reacting D-phenyl alanine with a solution of thionyl chloride in a $C_{1-4}$alcohol, preferably methanol, to give the corresponding alkyl ester of formula (II), preferably the methyl ester, as the hydrochloride salt, which is then reacted directly with trans-4-isopropylcyclohexanecarboxylic acid of above formula (III) in the presence of a dehydrating agent, such as N,N'-dicyclohexylcarbodiimide, 1-hydroxybenzotriazole or the like, and a base, such as triethylamine or the like, to give the above described $C_{1-4}$ alkyl ester of nateglinide of formula (IV), preferably the methyl ester of nateglinide. The thus obtained $C_{1-4}$ alkyl ester of nateglinide of formula (IV) is then preferably subjected to alkali hydrolysis, without isolation, and subsequent acidification to yield nateglinide. Suitably, where the alkali employed is sodium hydroxide, this provides nateglinide in the form of its sodium salt, which is then subjected to acidification as referred to above.

Preferably a process according to the above described preferred first embodiment of the present invention can be represented by the reaction scheme shown in FIG. 1.

According to a preferred second embodiment of the present invention, a process as provided thereby further comprises initially reacting D-phenyl alanine with a solution of thionyl chloride in a $C_{1-4}$alcohol, preferably methanol, to give the corresponding alkyl ester of formula (II), preferably the methyl ester, as the hydrochloride salt, which is converted in situ to the free base suitably using aqueous ammonia, and then reacted with trans-4-isopropylcyclohexanecarboxylic acid of above formula (III) in the presence of a dehydrating agent, such as N,N'-dicyclohexylcarbodiimide, 1-hydroxybenzotriazole or the like, to give the above described $C_{1-4}$ alkyl ester of nateglinide of formula (IV), preferably the methyl ester of nateglinide. The thus obtained $C_{1-4}$ alkyl ester of nateglinide of formula (IV) is then preferably subjected to alkali hydrolysis, without isolation, and subsequent acidification to yield nateglinide. Suitably, where the alkali employed is sodium hydroxide, this provides nateglinide in the form of its sodium salt, which is then subjected to acidification as referred to above.

Figure 2:
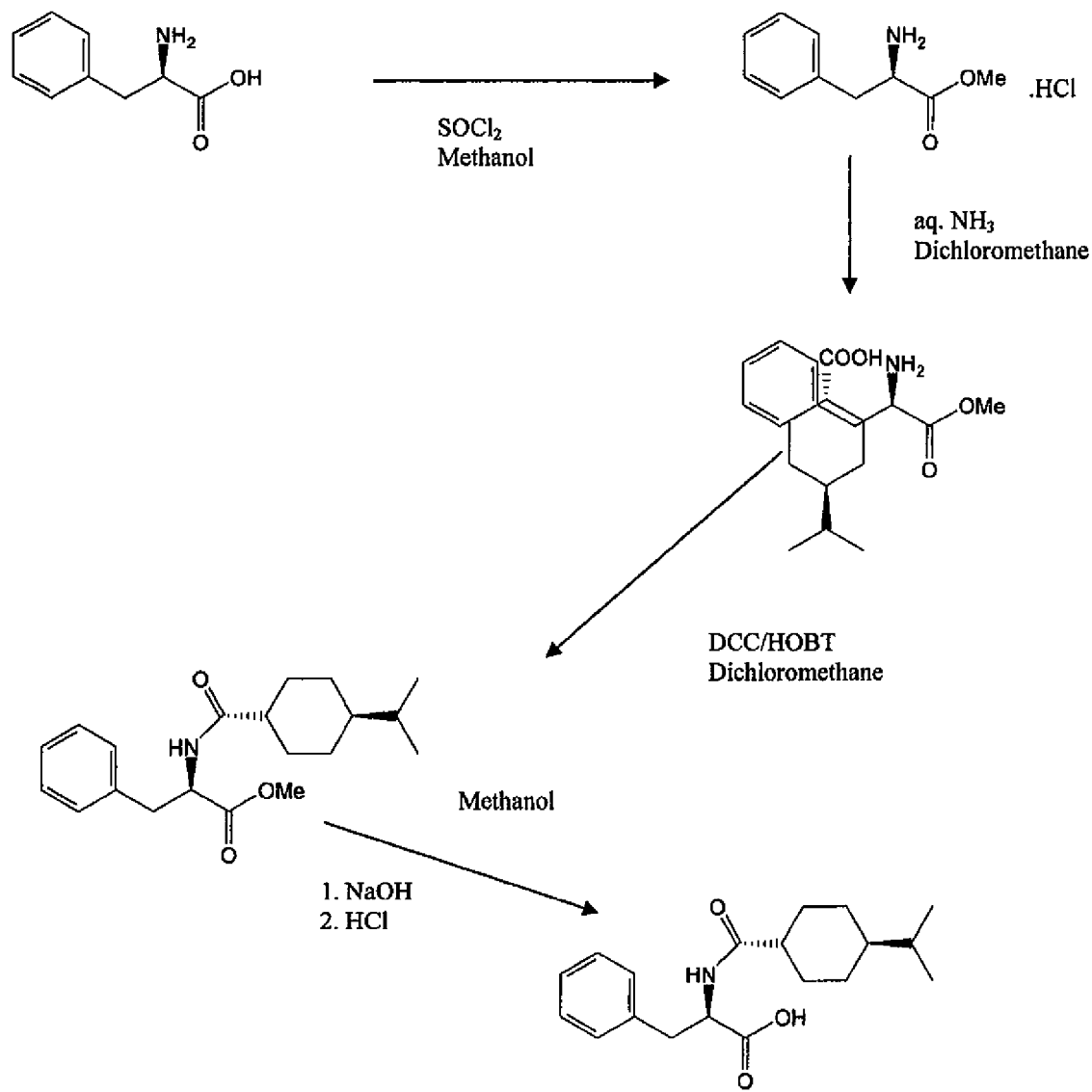

Preferably a process according to the above described preferred second embodiment of the present invention can be represented by the reaction scheme shown in FIG. 2.

According to a preferred third embodiment of the present invention, a process as provided thereby further comprises initially reacting D-phenyl alanine with a solution of thionyl chloride in a $C_{1-4}$alcohol, preferably methanol, to give the corresponding alkyl ester of formula (II), preferably the methyl ester, as the hydrochloride salt, which is converted in situ to the free base suitably using aqueous ammonia, and then reacted with trans-4-isopropylcyclohexanecarboxylic acid halide of above formula (III), preferably trans-4-isopropylcyclohexanecarboxylic acid chloride, in the presence of base such as triethylamine and N,N-dimethylamino pyridine (DMAP), to give the above described $C_{1-4}$ alkyl ester of nateglinide of formula (IV), preferably the methyl ester of nateglinide. The thus obtained $C_{1-4}$ alkyl ester of nateglinide of formula (IV) is then preferably subjected to alkali hydrolysis, without isolation, and subsequent acidification to yield nateglinide. Suitably, where the alkali employed is sodium hydroxide, this provides nateglinide in the form of its sodium salt, which is then subjected to acidification as referred to above.

Figure 3:
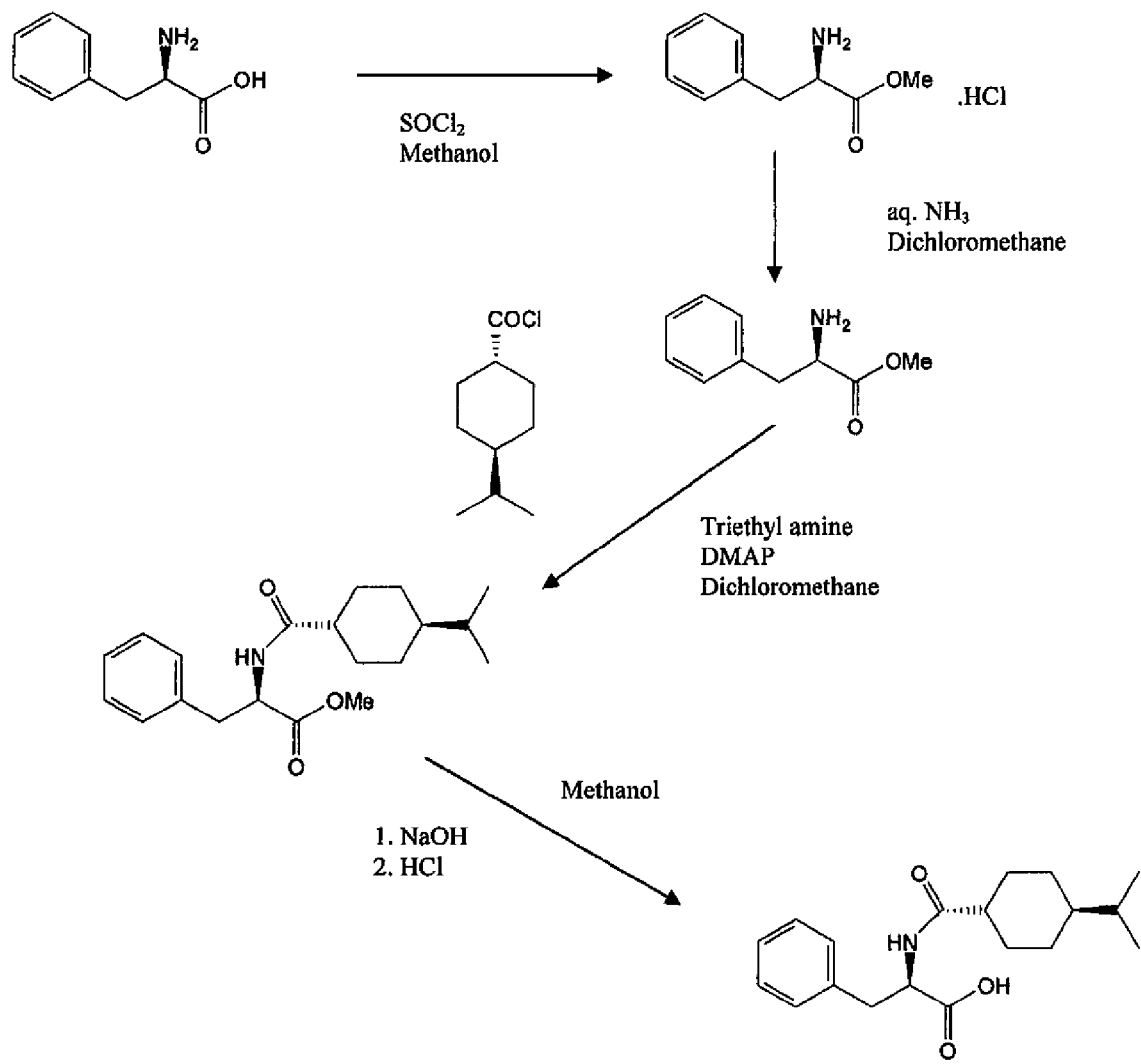

Preferably a process according to the above described preferred third embodiment of the present invention can be represented by the reaction scheme shown in FIG. 3.

A process according to the present invention desirably further comprises purification of nateglinide by one or more solvent washes. After the above described reaction of an alkyl ester of D-phenylalanine of formula (II) with trans-4-isopropylcyclohexanecarboxylic acid or trans-4-isopropylcyclohexanecarboxylic acid halide of formula (III), the reaction solution containing the alkyl ester of nateglinide of formula (IV) is preferably washed with NaOH solution (typically 5%) to remove trans-4-isopropyl cyclohexanecarboxylic acid or trans-4-isopropylcyclohexanecarboxylic acid halide and other acid impurities. Furthermore, after the above described hydrolysis step to yield nateglinide of formula (I), purification of nateglinide from the methyl ester of nateglinide of formula (Ia) is preferably accomplished by washing the reaction mass comprising nateglinide with organic solvents typically selected from the group of water immiscible organic solvents. Preferably, the aqueous phase on acidification substantially as hereinbefore described yields nateglinide as white crystalline solid with total impurities being present at less than about 0.1%, with an overall yield of about 75%.

According to the present invention, there is, therefore, further provided a one-pot process for the preparation of nateglinide, which process comprises reacting an alkyl ester of D-phenylalanine of formula (II):

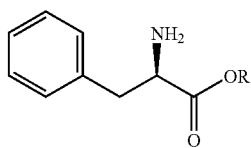
(II)

where R represents $C_{1-4}$alkyl, typically methyl, either as the free base or in salt form (typically the hydrochloride), with trans-4-isopropylcyclohexanecarboxylic acid or trans-4-isopropylcyclohexanecarboxylic acid halide of formula (III)

(III)

where X represents hydroxy or halo, typically chloro, to obtain a $C_{1-4}$ alkyl ester of nateglinide of formula (IV), preferably the methyl ester of nateglinide

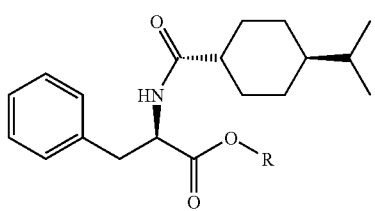
(IV)

wherein the reaction solution containing the above $C_{1-4}$ alkyl ester of nateglinide of formula (IV) is washed with NaOH solution (typically 5%) to remove trans-4-isopropyl cyclohexanecarboxylic acid and other acid impurities, followed by alkali hydrolysis to yield nateglinide of formula (I)

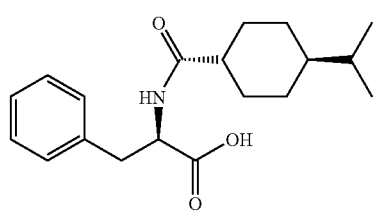
(I)

wherein the resulting reaction mass comprising nateglinide of formula (I) is washed with one or more water immiscible organic solvents, followed by acidification to yield crystalline nateglinide of formula (I).

The main advantages of the process of the present invention are that (a) there is no isolation of any intermediate (b) the processing time is reduced (c) it does not require any activation of the intermediate trans-4-isopropylcyclohexanecarboxylic acid and (d) the product obtained from the process does not require additional purification and/or crystallization.

The present invention further provides nateglinide prepared by a process as hereinbefore described.

Nateglinide as provided by the present invention is useful as a hypoglycemic agent in the treatment of Type II diabetes mellitus.

The present invention accordingly provides, therefore, for use in therapy nateglinide as provided by a process according to the present invention substantially as hereinbefore described.

Accordingly, the present invention provides for use in the treatment of and/or prophylaxis of hypoglycemia, nateglinide as provided by a process according to the present invention. In particular, there is provided nateglinide as provided by a process according to the present invention for use in the treatment of diabetes mellitus.

Accordingly, the present invention also provides a pharmaceutical composition comprising nateglinide as provided by a process according to the present invention, and a pharmaceutically acceptable carrier therefor. Preferably a composition as provided by the present invention can be for oral administration. The pharmaceutical compositions of the invention may, however, be administered in any suitable way and in any suitable form, for example orally in the form of tablets, capsules, liquid preparations, granules, lozenges, or parenterally in the form of injectable, or infusible, solutions or suspensions.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents can comprise: corn starch, potato starch, talcum, magnesium stearate, gelatine, lactose, gums, and the like. Any other adjuvant or additive colourings, aroma, preservatives or the like may also be used provided that they are compatible with the nateglinide as provided by the present invention.

Solutions for injections may be prepared by dissolving nateglinide as provided by the present invention and possible additives in a part of the solvent for injection, typically sterile water, adjusting the solution to the desired volume, sterilisation of the solution and filling in suitable ampoules or vials. Any suitable additive conventionally used in the art may be added, such as tonicity agents, preservatives, antioxidants and the like.

The present invention further provides a method for the treatment and/or prophylaxis of hypoglycemia in a patient, which method comprises administering a therapeutically effective amount of nateglinide as provided by a process according to the present invention to a hypoglycemic patient in need thereof. In particular, the present invention provides a method for the treatment and/or prophylaxis of diabetes mellitus in a patient, which method comprises administering a therapeutically effective amount of nateglinide as provided by a process according to the present invention to a patient suffering from, or susceptible to, diabetes mellitus.

In a further aspect the present invention provides the use of nateglinide as provided by a process according to the present invention, for the manufacture of a medicament for the treatment and/or prophylaxis of hypoglycemia. In particular, the present invention provides use of nateglinide as provided by a process according to the present invention for the manufacture of a medicament for the treatment and/or prophylaxis of diabetes mellitus.

The particular dosage form of nateglinide as provided by the present invention required for therapeutic use or treatment in accordance with the present invention will depend on the particular disease state being treated, and the symptoms and severity thereof. Dosage, routes of administration, and frequency of dosing are best decided by an attending physician.

EXAMPLES

The present invention is further illustrated by the following Examples, which do not limit the scope of the invention in any way.

Example 1

To well stirred methanol (4 lit), previously cooled (to 0° C.) thionyl chloride (400 ml) was added drop wise below 10° C. D-phenyl alanine (400 gms) was added and allowed to react as the temperature was raised to 25° C., with stirring for 24 hours. After completion of reaction, methanol was distilled off, and replaced with dichloromethane (1 lit) after cooling to ambient temperature. The contents were then basified with aq. ammonia (600 ml), the organic layer was separated and the aqueous layer was back extracted (500 ml). The combined organic layer was dried over sodium sulfate, filtered and 1-hydroxybenzotriazole (140 gms) was added and stirred to obtain a clear solution at ambient temperature.

The resulting solution was then cooled to 0° C. and trans-4-isopropylcyclohexanecarboxylic acid (355 gms) was added in one addition. A solution of N,N'-dicyclohexylcarbodiimide (500 gms) in dichloromethane (1 lit) was added drop wise in 60 minutes below 5° C. The reaction mass was then agitated at 15° C. for 3 hours, filtered through celite, and the filtrate was washed with 5% NaOH (1 lit) solution twice followed by water wash to obtain neutral pH. The organic layer was then distilled at atmospheric pressure replacing with methanol (2.6 lit) and the separated white solid was cooled to 25° C. To this suspension 10% NaOH solution (950 ml) was added below 30° C. in 30 minutes. The reaction mass was then stirred for 15 hours at 20-25° C. until a clear solution was obtained. After completion of the reaction, water (4 lit) was added and the bulk of methanol was vacuum distilled.

The above aqueous layer was further washed with dichloromethane (500 ml×2), treated with charcoal, filtered through celite and 6N hydrochloric acid was added to the filtrate until at a pH of 2-3 at 25° C. a thick white precipitate of nateglinide separated out. This was then stirred for 30 minutes, filtered and washed with water until neutral pH. The obtained solid was dried at 80° C. to obtain nateglinide (475 gms) as white crystalline solid (HPLC purity 99.6%, no impurity greater than 0.1%, melting point 128-131° C.).

Example 2

To well stirred methanol (4 lit) previously cooled (to 0° C.) thionyl chloride (400 ml) was added drop wise below 10° C. D-phenyl alanine (400 gms) was added and allowed to react as the temperature was raised to 25° C. with stirring for 24 hours. After completion of reaction methanol was distilled off, and replaced with dichloromethane (1 lit) after cooling to ambient temperature. To this triethyl amine (400 ml) was added followed by 1-hydroxybenzotriazole (140 gms) and stirred to obtain a clear solution at ambient temperature.

The solution was then cooled to 0° C. and trans-4-isopropylcyclohexanecarboxylic acid (355 gms) was added in one addition. A solution of N,N'-dicyclohexylcarbodiimide (500 gms) in dichloromethane (1 lit) was added drop wise in 60 minutes below 5° C. The reaction mass was then agitated at 15° C. for 3 hours, filtered through celite, and the filtrate was washed with 5% NaOH solution (1 lit) twice followed by water wash until neutral pH. The organic layer was then distilled at atmospheric pressure replacing with methanol (2.6 lit) and separated white solid was cooled to 25° C. To this suspension 10% NaOH solution (950 ml) was added below 30° C. in 30 minutes. This was then stirred for 15 hours until a clear solution was obtained at 20-25° C. After completion of the reaction water (4 lit) was added and the bulk of methanol was vacuum distilled.

The above aqueous layer was further washed with dichloromethane (500 ml×2), treated with charcoal, filtered through celite and 6N hydrochloric acid was added to the filtrate until a pH 2-3 at 25° C. was obtained and a thick white precipitate of nateglinide separated out. This was then stirred for 30 minutes, filtered and washed with water until neutral pH. The obtained solid was dried at 80° C. to obtain nateglinide (460 gms) as white crystalline solid (HPLC purity 99.7%, no impurity greater than 0.1%, melting point 128-131° C.).

Example 3

To well stirred methanol (4 lit) previously cooled (to 0° C.) thionyl chloride (400 ml) was added drop wise below 10° C. D-phenyl alanine (400 gms) was added and allowed to react as the temperature was raised to 25° C. with stirring for 24 hours. After the completion of reaction methanol was distilled off, and replaced with dichloromethane (2 lit) after cooling to ambient temperature. To this triethylamine (800 ml) and N,N-dimethylaminopyridine (25 gms) were added followed by a solution of trans-4-isopropylcyclohexanecarboxylic acid chloride (400 gms) in dichloromethane (1 lit) added drop wise at 0 to 5° C. This was then stirred at ambient temperature for 18 hours. The organic layer was then washed with saturated bicarbonate solution (500 ml×2), 1 N HCl (500 ml×2) and water. The organic layer was the dried over sodium sulfate and then distilled at atmospheric pressure replacing with methanol (2.6 lit) and separated white solid was cooled to 25° C. To this suspension 10% NaOH (950 ml) solution was added below 30° C. in 30 minutes, stirred for 15 hours at 20-25° C. until a clear solution was obtained. After completion of the reaction, water (4 lit) was added and the bulk of methanol was vacuum distilled.

The above aqueous layer was further washed with dichloromethane (500 ml×2), treated with charcoal, filtered through celite and 6N hydrochloric acid was added to the filtrate until a pH of 2-3 was obtained at 25° C., when a thick white precipitate of nateglinide separated out. This was then stirred for 30 minutes, filtered and washed with water until a neutral pH was obtained. The obtained solid was dried at 80° C. to obtain nateglinide (480 gms) as white crystalline solid (HPLC purity 99.6%, no impurity greater than 0.1%, melting point 128-131° C.).

The invention claimed is:
1. A one-pot for the preparation of nateglinide, which process comprises (1) reacting a mixture consisting essentially of a dehydrating agent, a base, an alkyl ester of D-phenylalanine of formula (II):

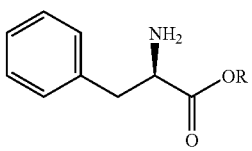

where R represents $C_{1-4}$ alkyl, and trans-4-isopropylcyclohexanecarboxylic acid or trans-4-isopropylcyclohexanecarboxylic acid halide of formula (III):

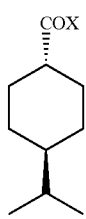

where X represents hydroxy or halo, to obtain a $C_{1-4}$ alkyl ester of nateglinide of formula (IV):

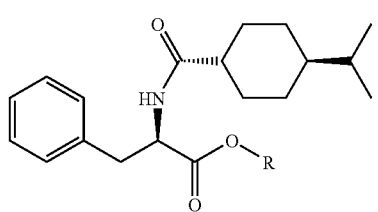

(2) followed by hydrolysis to yield nateglinide of formula (I):

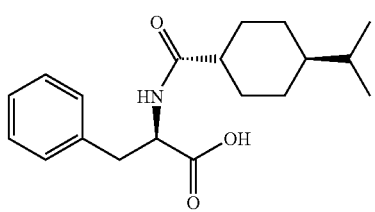

wherein the step (1) comprises initially reacting D-phenyl alanine with a solution of thionyl chloride in a $C_{1-4}$ alcohol to give the corresponding alkyl ester of formula (II) as the hydrochloride salt, which is converted in situ to the free base which is then reacted with trans-4-isopropylcyclohexanecarboxylic acid or trans-4-isopropylcyclohexanecarboxylic acid halide of above formula (III) in the presence of a dehydrating agent and wherein said in situ conversion is carried out using a base comprising aqueous ammonia.

2. The process according to claim 1, wherein R in formulae (II) and (IV) represents methyl.

3. The process according to claim 1, wherein said dehydrating agent comprises N,N'-dicyclohexylcarbodiimide/1-hydroxyzotriazole.

4. The process according to claim 1, wherein said $C_{1-4}$ alkyl ester of nateglinide of formula (IV) is subjected to alkali hydrolysis, without isolation, and subsequent acidification to yield nateglinide.

5. The process according to claim 4, wherein said alkali is sodium hydroxide.

6. The process according to claim 5, wherein hydrolysis with said sodium hydroxide provides nateglinide in the form of its sodium salt, which is then subjected to acidification to yield nateglinide.

7. The process according to claim 1, which further comprises purification of nateglinide by one or more solvent washes.

8. The process according to claim 7, wherein following reaction of said alkyl ester of D-phenylalanine of formula (II) with trans-4-isopropylcyclohexanecarboxylic acid or trans-4-isopropylcyclohexanecarboxylic acid halide of formula (III), the reaction solution containing the alkyl ester of nateglinide of formula (IV) is washed with NaOH solution to remove trans-4-isopropyl cyclohexanecarboxylic acid or trans-4-isopropylcyclohexanecarboxylic acid halide and other acid impurities.

9. The process according to claim 7, wherein the solvent washes comprise one or more water immiscible organic solvents.

10. A one-pot process for the preparation of nateglinide comprising:
   reacting D-phenyl alanine with thionyl chloride to give a hydrochloride salt of a methyl ester of D-phenyl alanine;
   reacting a mixture consisting essentially of the hydrochloride salt of the methyl ester of D-phenyl alanine with trans-4-isopropylcyclohexanecarboxylic acid in the presence of (i) dehydrating agent comprising N,N'-dicyclohexylcarbodiimide or 1-hydroxybenzotriazole and (ii) triethylamine to give a methyl ester of nateglinide;
   subjecting the methyl ester of nateglinide to alkali hydrolysis in the presence of methanol and sodium hydroxide to yield a reaction mixture; and
   contacting the reaction mixture with hydrochloric acid to yield nateglinide wherein the methyl ester of nateglinide is subjected to alkali hydrolysis without isolation.

11. A one-pot process for the preparation of nateglinide comprising:
   reacting D-phenyl alanine with thionyl chloride to give a hydrochloride salt of a methyl ester of D-phenyl alanine;
   converting the hydrochloride salt of the methyl ester of D-phenyl alanine to a free base;
   reacting a mixture consisting essentially of the free base with trans-4-isopropylcyclohexanecarboxylic acid in the presence of a dehydrating agent to give a methyl ester of nateglinide;
   subjecting the methyl ester of nateglinide to alkali hydrolysis in the presence of methanol and sodium hydroxide to yield a reaction mixture; and
   contacting the reaction mixture with hydrochloric acid to yield nateglinide wherein the free base is subjected to alkali hydrolysis without isolation.

12. A one-pot process for the preparation of nateglinide comprising:
   reacting D-phenyl alanine thionyl chloride to give a hydrochloride salt of a methyl ester of D-phenyl alanine;
   contacting the hydrochloride salt of the methyl ester of D-phenyl alanine with aqueous ammonia in dichloromethane to produce a free base of the methyl ester of D-phenyl alanine;
   reacting a mixture consisting essentially of the free base of the methyl ester of D-phenyl alanine with trans-4-isopropylcyclohexanecarboxylic acid chloride, triethylamine and N,N-dimethylamino pyridine in a dichloromethane to yield a methyl ester of nateglinide;

subjecting the methyl ester of nateglinide to alkali hydrolysis in the presence of methanol and sodium hydroxide to yield a reaction mixture; and contacting the reaction mixture with hydrochloric acid to yield nateglinide wherein the free base is subjected to alkali hydrolysis without isolation.

* * * * *

UNITED STATES PATENT AND TRADEMARK OFFICE
CERTIFICATE OF CORRECTION

| | | |
|---|---|---|
| PATENT NO. | : 8,658,821 B2 | Page 1 of 1 |
| APPLICATION NO. | : 11/570405 | |
| DATED | : February 25, 2014 | |
| INVENTOR(S) | : Kankan et al. | |

It is certified that error appears in the above-identified patent and that said Letters Patent is hereby corrected as shown below:

In the Claims:

Column 10, Line 64, replace "A one-pot" with --A one-pot process--

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,658,821 B2                                             Page 1 of 1
APPLICATION NO. : 11/570405
DATED            : February 25, 2014
INVENTOR(S)      : Kankan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1870 days.

Signed and Sealed this
Twenty-ninth Day of September, 2015

Michelle K. Lee
*Director of the United States Patent and Trademark Office*